(12) United States Patent
Arieli et al.

(10) Patent No.: US 9,757,027 B2
(45) Date of Patent: Sep. 12, 2017

(54) SYSTEM AND METHOD FOR PERFORMING TEAR FILM STRUCTURE MEASUREMENT AND EVAPORATION RATE MEASUREMENTS

(71) Applicant: ADOM, Advanced Optical Technologies Ltd, Lod (IL)

(72) Inventors: Yoel Arieli, Jerusalem (IL); Yoel Cohen, Nes Ziona (IL); Shlomi Epstein, Jerusalem (IL); Dror Arbel, Tzur Itzhak (IL); Ra'anan Gefen, Reut (IL)

(73) Assignee: ADOM, Advanced Optical Technologies Ltd. (IL)

( * ) Notice: Subject to any disclaimer, the term of this patent is extended or adjusted under 35 U.S.C. 154(b) by 0 days.

(21) Appl. No.: 15/227,839

(22) Filed: Aug. 3, 2016

(65) Prior Publication Data
US 2016/0338585 A1 Nov. 24, 2016

Related U.S. Application Data

(63) Continuation-in-part of application No. PCT/IL2015/050232, filed on Mar. 4, 2015.
(Continued)

(51) Int. Cl.
| | |
|---|---|
| *A61B 3/14* | (2006.01) |
| *A61B 3/10* | (2006.01) |
| *G01B 9/02* | (2006.01) |
| *G01B 11/06* | (2006.01) |
| *A61B 3/00* | (2006.01) |
| *A61B 3/15* | (2006.01) |

(Continued)

(52) U.S. Cl.
CPC ............ *A61B 3/101* (2013.01); *A61B 3/0025* (2013.01); *A61B 3/1005* (2013.01); *A61B 3/152* (2013.01); *G01B 9/0209* (2013.01); *G01B 9/02021* (2013.01); *G01B 9/02025* (2013.01); *G01B 9/02027* (2013.01); *G01B 9/02044* (2013.01); *G01B 9/02087* (2013.01); *G01B 11/06* (2013.01); *G01B 11/0625* (2013.01); *G01B 11/0675* (2013.01); *G01N 21/274* (2013.01); *G02B 3/08* (2013.01); *G01B 2290/45* (2013.01); *G01N 2201/066* (2013.01); *G01N 2201/127* (2013.01)

(58) Field of Classification Search
CPC ..... A61B 3/1005; A61B 3/1015; A61B 3/107; A61B 3/14
USPC ................. 351/246, 221, 206, 205, 211, 212
See application file for complete search history.

(56) References Cited

U.S. PATENT DOCUMENTS

2013/0050648 A1* 2/2013 Steinmueller .......... A61B 3/107
351/206

* cited by examiner

*Primary Examiner* — Hung Dang
(74) *Attorney, Agent, or Firm* — Workman Nydegger

(57) ABSTRACT

A system and method are described for performing tear film structure measurement. A broadband light source illuminates the tear film. A spectrometer measures respective spectra of reflected light from at least one point of the tear film. A color camera performs large field of view imaging of the tear film, so as to obtain color information for all points of the tear film imaged by the color camera. A processing unit calibrates the camera at the point measured by the spectrometer so that the color obtained by the camera at the point matches the color of the spectrometer at the same point. The processing unit determines, from the color of respective points of the calibrated camera, thicknesses of one or more layers of the tear film at the respective points. Other applications are also described.

24 Claims, 6 Drawing Sheets

Related U.S. Application Data

(60) Provisional application No. 61/948,579, filed on Mar. 6, 2014.

(51) Int. Cl.
    *G01N 21/27*     (2006.01)
    *G02B 3/08*     (2006.01)

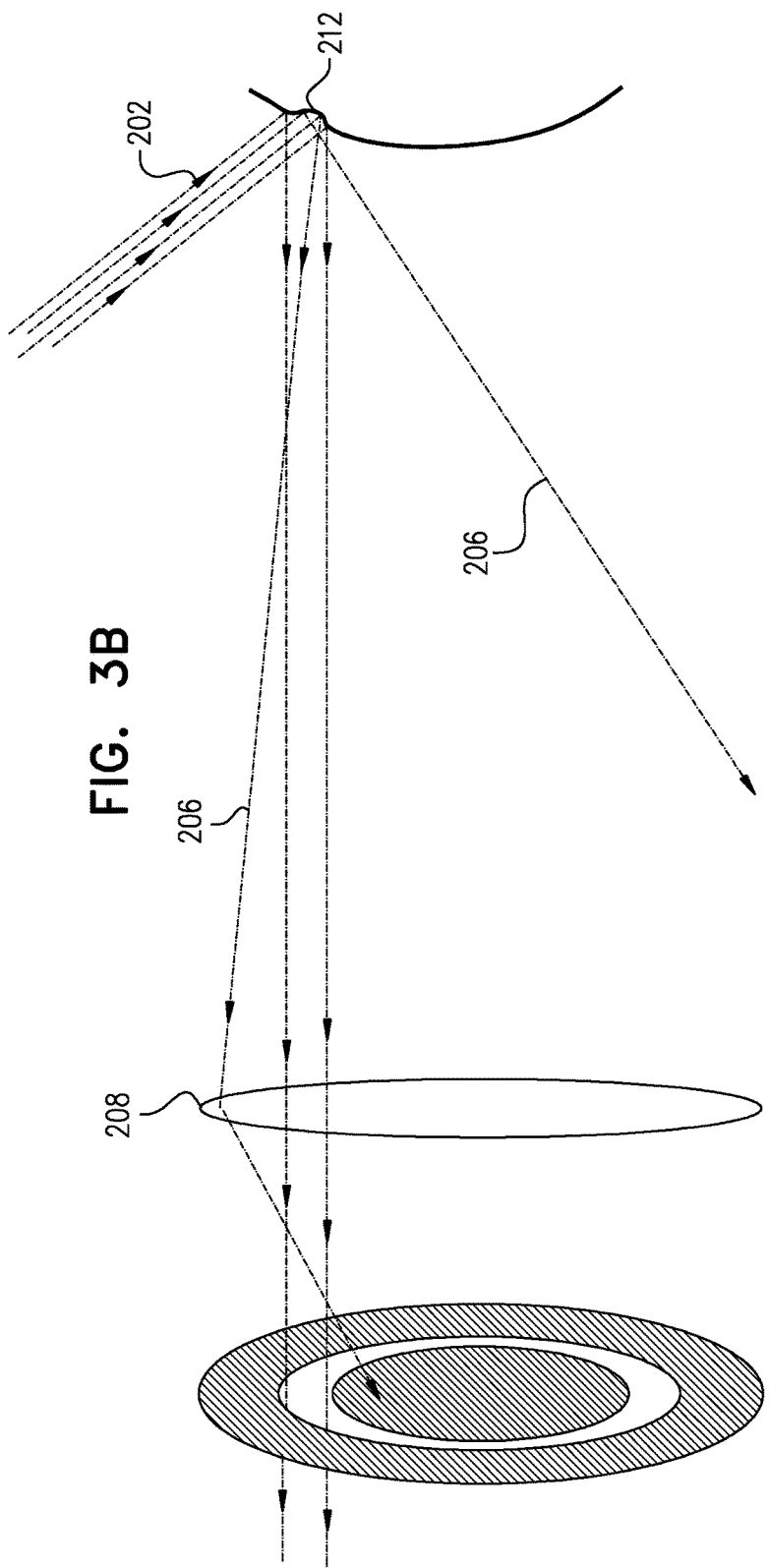

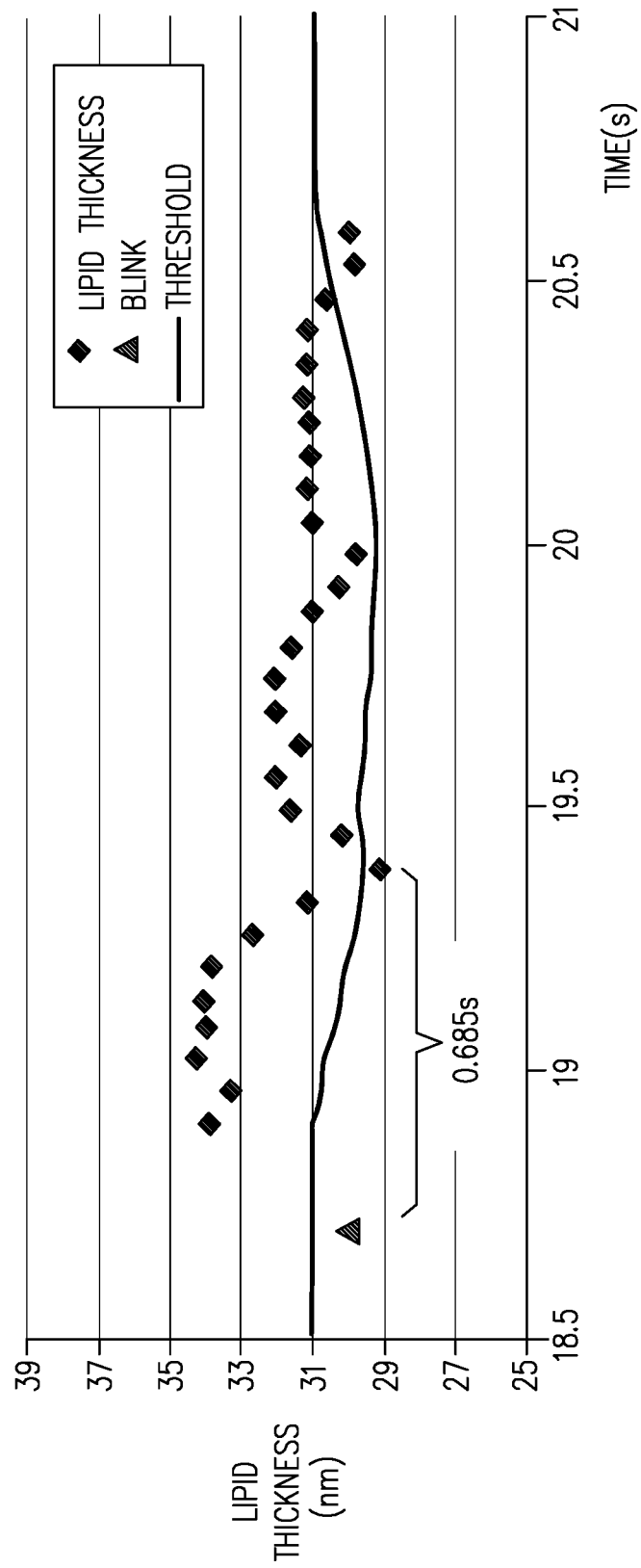

SYSTEM AND METHOD FOR PERFORMING TEAR FILM STRUCTURE MEASUREMENT AND EVAPORATION RATE MEASUREMENTS

CROSS-REFERENCE TO RELATED APPLICATIONS

The present application is a continuation-in-part of International Application No. PCT/IL2015/050232 to Arieli (published as WO 15/132788), filed Mar. 4, 2015, which claims priority from U.S. Provisional Application No. 61/948,579 to Cohen, filed Mar. 6, 2014. Both of the aforementioned applications are incorporated herein by reference.

FIELD OF EMBODIMENTS OF THE INVENTION

The present invention relates to optical layers measurements, and more particularly, to a method and apparatus for measuring the layers of the tear film.

BACKGROUND

In recent years, the diagnosis of dry eye has become an important subject of ophthalmologic diagnosis.

The diagnosis is conventionally performed by vital staining test, but this test requires the use of chemical eye drops and is painful to the examinee.

There are several methods for diagnosis of dry eye without contact.

U.S. Pat. No. 6,299,305 to Miwa describes an ophthalmic apparatus for measuring the dryness of a cornea of an eye to be examined by projecting light onto the cornea and detecting the reflected light from the tear film. The device measures the time-varying signal to determine the changes in the dryness of tear film. The signal is the fluorescence light reflected by a fluorescein being spread over the tear film.

At J. Opt. Soc. Am. A, 15, 268-275; IOVS, October 2000, 41, 11, 3348-3359 and IOVS, January 2003, 44, 1, 68-77 describe wavelength-dependent optical interferometers that have been developed for in-vivo aqueous tear film and contact lens thickness analysis. The instruments described in the publications are of similar design and are capable of measuring the thickness of the pre-corneal or pre-lens tear film aqueous+lipid layer thickness, post-lens tear film aqueous thickness among contact lens, contact lens thickness and corneal epithelial thickness. The instruments can also measure the thinning or thickening rates of the various tear film layers during normal blinking and between blinks or over time.

According to the described approach, the light reflections from the ocular surface arise from the combined aqueous+lipid layer and the lipid layer alone since the wavelength-dependent fringes from the aqueous layer only cannot be observed. Thus, the tear lipid layer thickness needs to be measured separately and subtracted from the combined aqueous+lipid thickness to derive aqueous-only layer thickness. This approach does not take into account the other layers above or below the aqueous layer such as the lipid layer and the microvilli Mucin layer. It also does not take into account the possible interaction between all the layers in the stack, their combined interference and their relative intensities. In order to have a proper and an accurate measurement one must use a suitable physical model that takes all interfaces reflections and interference into account.

The wavelength-dependent oscillations are created by the interactions of all combinations of reflections from the combined Microvilli height+aqueous+lipid layers, so that many interference frequencies can co-exist simultaneously. In the case of very thin layers whose thickness is the order of the wavelength of the light, such interference cannot be simply deduced from the power density due to resolution limits and there is a need to measure the absolute reflection changes across the spectrum and apply proper physical modeling. The model also must take into account the scattering of light from the lower interface below the aqueous layer and the gradient change of the Mucins concentration that creates gradual optical properties changes. In addition, the optical setup described, does not work in optimal conditions to measure the tear layers. Other important aspects of the system such as measuring the evaporation rate and auto-focusing with fast feedback to allow reasonable measurement success rate after small movements or blinking, are missing.

In J. Opt. Soc. Am. A, 23, 9, 2097-2103, 2006, a method for recording interference images from the full thickness of the precorneal tear film (PCTF) is described. Simultaneous images are recorded by two video cameras. One camera responds to broadband spectral illumination and records interference from the superficial lipid layer of the tear film while the other camera uses narrowband illumination and records interference from both the lipid layer and the full thickness of the PCTF. Thus the full-thickness interference fringes are derived from the difference between the narrowband and the broadband images. In this methodology the low amplitude reflection from the aqueous layer is derived from the narrowband light. However there is no indication about the absolute values of the thickness since the fringe contrast is an indication only for quarter wavelength change in the full thickness.

US 2008/0273171 to Huth describes a method of diagnosing dry eye by taking multiple measurements from a single point of the subject's eye. Each measurement uses an interferometer and calculates the thicknesses of the aqueous and the lipid layers by comparing the reflection of light from the eye to reflection calculated by an empirical equation. The same equation can also be used to measure the thickness of the lipid layer, thus, aqueous-only layer thickness is calculated by subtracting the measured lipid-only layer thickness from the combined aqueous+lipid layer thickness. However, in this procedure there is no impact to the existence of under layers or lower interface properties such as the epithelial or microvilli structures thus the confidence levels for the accurate values obtained are questionable.

US 2009/0225276 to Suzuki describes a method to measure the amount of tear fluid. A low magnification light source illuminates the outermost layer of a tear film on the cornea of a subject's eye. The interference stripes pattern created by the lipid film on the cornea is displayed on a monitor. To measure the amount of tear fluid, different light-emitting elements of a high-magnification light source are used to irradiate the tear fluid meniscus that has accumulated on the lower eyelid portion of the anterior ocular segment. The light reflected from the surface of the meniscus forms separated images of the light-emitting elements on a monitor with some interval between the images. The amount of tear fluid can be quantitatively measured by measuring the interval between the images. This method relies on the connection between the meniscus and the center of the cornea and therefore suffers from inaccuracy.

In US 2012/0300174 to Yokoi the tear film lipid layer on a cornea of an eye is described as being illuminated by a white light source and is imaged by a color camera. The image of the tear film lipid layer is processed, and the initial spread speed of the tear film lipid layer and the time until the tear film lipid layer is broken are measured.

In U.S. Pat. No. 7,281,801 to Wang the thickness and the dynamics of a tear film layer and the heights of tear menisci around upper and lower eyelids of an eye are described as being measured by acquiring a plurality of images between consecutive blinks of the eye using optical coherence tomography (OCT). The plurality of reflectivity profiles from the OCT images are aligned and averaged and the difference between a first peak and a second peak of the average reflectivity profile is measured to determine the thickness of the tear film layer. This method relies on the connection between the meniscus and the center of the cornea and therefore suffers from inaccuracy.

In U.S. Pat. No. 8,192,026 to Gravely the relative thickness of the lipid layer component of the precorneal tear film on the surface of an eye is described as being measured by illuminating the eye using a Lambertian broad spectrum light source covering the visible region. The light is specularly reflected from the lipid layer and undergoes constructive and destructive interference in the lipid layer. The specularly reflected light is collected and the interference patterns on the tear film lipid layer are imaged on to a high resolution video monitor. The lipid layer thickness is classified on the basis of the most dominant color present in the interference pattern. This method suffers from basic problems of "2-π ambiguity" or "order skip" and thus prevents uniqueness of the measurement.

Thus, there is required a simple and reliable method and system that can accurately measure both the lipid and the aqueous layers, two dimensionally to enable the determination of the evaporation rates required for diagnosing dry eye phenomena.

SUMMARY OF EMBODIMENTS

It is therefore an object of the present invention to provide a simple and reliable optical system and method that can measure the lipid and the aqueous layers in large area.

This object is realized according to the invention by a system and method having the features of the respective independent claims.

According to the one embodiment of the present invention a combination of a spectrometer and an interferometer is used for measuring the lipid and the aqueous layers in large area where the measurement accuracy and speed are also suitable for the measurement of the evaporation rate.

According to another embodiment of the present invention a combination of a spectrometer and a color camera is used for measuring the lipid and the aqueous layers in large area.

According to another embodiment of the present invention a spectrometer is used to measure the Microvili depth and Mucin gradient profile.

According to another embodiment of the present invention the combination of a spectrometer and color camera is used for measuring the lipid continuity and break up time.

There is further provided, in accordance with some applications of the present invention, a system for performing tear film structure measurement, the system including:

a broadband light source configured to illuminate the tear film;

a spectrometer for measuring respective spectra of reflected light from at least one point of the tear film;

a color camera configured for large field of view imaging of the tear film so as to obtain color information for all points of the tear film imaged by the color camera; and a processing unit coupled to the camera and to the spectrometer and configured for (i) calibrating the camera at the at least one point measured by the spectrometer so that the color obtained by the camera at said at least one point matches the color of the spectrometer at the same point, and (ii) determining from the color of respective points of the calibrated camera thicknesses of one or more layers of the tear film at the respective points.

In some applications, the system further includes a flat objective Fresnel lens that is configured to converge a large range of angles to a point and is disposed a short distance from the tear film.

In some applications, the system further includes an autofocusing mechanism for focusing the color camera and the spectrometer.

In some applications, the system further includes a mechanism for centering a cornea of the subject onto optical axes of the spectrometer and the color camera, the mechanism including a projector that is configured to project a given pattern onto the subject's cornea.

In some applications, the spectrometer is configured to measure the respective spectra of reflected light from the at least one point of the tear film using a measurement time of between 20 and 300 milliseconds.

In some applications, the system further includes an aperture that is configured to facilitate detection of tear film sub-micron level surface topography by causing narrow angles of the reflected light to be received by the color camera.

In some applications, the processing unit is further configured to compute respective rates of change of thicknesses of the one or more layers of the tear film at different points along the tear film obtained over a known time interval.

In some applications, the system further includes one or more optical elements selected from the group consisting of: lenses, Fresnel lenses, annular aperture filters, polarizers, spatial light modulators (SLMs), and diffractive optical elements (DOEs).

In some applications, the system further includes an interferometer having a pair of mirrors disposed in a path selected from the group consisting of: an illumination path of the system and an imaging path of the system, and configured to modulate the spectrum of the light source by changing the optical path difference between the mirrors.

In some applications, the interferometer includes a spatial light modulator (SLM) disposed in an arm thereof.

In some applications, the processing unit is coupled to the interferometer and configured for (i) calibrating consecutively the interferometer by computing the optical path difference between the mirrors of the interferometer at at least one of the points measured by the spectrometer, (ii) using the calibrated interferometer to modulate the spectrum of the light source by changing the optical path difference between its mirrors, (iii) obtaining a calibrated interferogram at respective points of the tear film, and (iv) using the calibrated interferogram to determine thickness of one or more layers of the tear film at the respective points.

In some applications, the spectrometer further includes a deflecting element for scanning different tear film locations.

In some applications, the system further includes a narrow band filter between the light source and the camera for producing interference fringe patterns characteristic of different layers of the tear film.

In some application, the spectrometer is used to correlate a fringe pattern in a known location or pixel with a respective thickness of each layer of the tear film and thereby derive the respective thickness of each layer of the tear film without scanning the tear film.

In some applications, the spectrometer is configured to measure the respective spectra of reflected light from the at least one point of the tear film using a measurement spot size of between 40 microns and 300 microns.

In some applications, the spectrometer is configured to measure the respective spectra of reflected light from the at least one point of the tear film using a measurement spot size of between 100 microns and 240 microns.

There is further provided, in accordance with some applications of the present invention, a method for performing tear film structure measurement, the method including:

illuminating the tear film with a broadband light source;

using a spectrometer to measure respective spectra of reflected light from at least one point of the tear film;

imaging on a color camera a large field of view image of the tear film so as to obtain color information for all points of the tear film;

calibrating the camera at the at least one point measured by the spectrometer so that the color obtained by the camera at said at least one point matches the color of the spectrometer at the same point; and determining from the color of respective points of the calibrated camera thicknesses of one or more layers of the tear film at the respective points.

In some applications, the method further includes computing respective rates of change of the thicknesses of the one or more layers of the tear film at different points along the tear film obtained over a known time interval.

In some applications, the method further includes:

(i) using a narrow band filter to obtain an interference pattern due to thickness non uniformity of the one or more layers of the tear film;

(ii) determining absolute values of the thicknesses of the one or more layers of the tear film at the overlapping locations of the interference pattern and spectrometer measurement points;

(iii) applying the absolute values at overlapping locations to determine the absolute values of the thicknesses at neighboring pixels that also have interference patterns.

In some applications, the method further includes using electromagnetic simulation in order to fit measurement results to a biological model of stack of tissues and liquid layers.

In some applications, the method further includes autofocusing the color camera and the spectrometer.

In some applications, using a spectrometer to measure respective spectra of reflected light from at least one point of the tear film includes using a measurement time of between 20 and 300 milliseconds for measurements performed by the spectrometer.

In some applications, the method further includes:

Fourier transforming the spectra of the reflected light so as to obtain, for each of point measured by the spectrometer, a respective interferogram; and using the interferograms to determine the thickness of the one or more layers of the tear film at the corresponding point.

In some applications, the method further includes computing a respective rate of change of the thicknesses of the one or more layers of the tear film at different points along the tear film obtained over a known time interval.

In some applications, the method further includes modulating a spectrum of the light source by changing an optical path difference between a pair of mirrors of an interferometer.

In some applications, the method further includes:

(i) calibrating the interferometer by computing the optical path difference between the mirrors of the interferometer at at least one of the points measured by the spectrometer, (ii) using the calibrated interferometer to modulate the spectrum of the light source by changing the optical path difference between the mirrors of the calibrated interferometer, (iii) using the measured reflected light to obtain a calibrated interferogram at respective points of the tear film, and (iv) using the calibrated interferogram to determine a thickness of the one or more layers of the tear film at the respective points.

In some applications, using a spectrometer to measure respective spectra of reflected light from at least one point of the tear film includes using a measurement spot size of between 40 microns and 300 microns.

In some applications, using a spectrometer to measure respective spectra of reflected light from at least one point of the tear film includes using a measurement spot size of between 100 microns and 240 microns.

There is further provided, in accordance with some applications of the present invention, a method including:

acquiring a plurality of measurements of a thickness of a layer of a tear film of an eye of a subject, using a measuring device selected from the group consisting of: a spectrometer, and an interferometer;

identifying a time period over which there is a change in the thickness of the layer of the tear film that has a negative correlation with time, the correlation having a correlation value that passes a threshold; and identifying a rate of thickness change of the layer by determining a rate of thickness change of the layer over the identified time period.

There is further provided, in accordance with some applications of the present invention, a method including:

acquiring a plurality of measurements of a thickness of a layer of a tear film of an eye of a subject over a given time period, using a measuring device selected from the group consisting of: a spectrometer, and an interferometer;

determining a stability level of the layer by determining a ratio between an indication of variance of the thickness over the given time period, and an average of the thickness over the given time period; and at least partially in response thereto, determining a level of the health of the tear film.

There is further provided, in accordance with some applications of the present invention, a method including:

acquiring a plurality of measurements of a thickness of a layer of a tear film of an eye of a subject, using a measuring device selected from the group consisting of: a spectrometer, and an interferometer;

subsequent to the subject having blinked, identifying that a breakup of the layer of the tear film has occurred, in response to determining the thickness of the layer has fallen below a threshold;

determining a breakup time, by measuring the time between the subject having blinked and the occurrence of the breakup event; and at least partially in response thereto, determining a level of health of the tear film.

In some applications, identifying that the breakup event has occurred further includes:

in response to identifying that a potential breakup event has occurred in a given area;

comparing a variance in the thickness of the layer in the given area to variances of thickness of the layer in areas that are in a vicinity of the area; and confirming that the breakup event has occurred at least partially in response thereto.

There is further provided, in accordance with some applications of the present invention, a method, for use with an optical system that includes a camera, the method including:

detecting surface topography of a portion of a curved surface of an object by:

directing a beam toward the surface from an angle of incidence of more than 50 degrees to an optical axis of the camera;

receiving light reflected from the surface with the camera, via a narrow-angle aperture; and using a computer processor:

detecting one or more darkened regions in the received light; and detecting the surface topography in response to the detected darkened regions.

In some applications, receiving light reflected from the surface with the camera, via the narrow-angle aperture includes receiving light reflected from the surface with the camera, via a narrow-angle aperture that defines an angle of less than 3 degrees.

In some applications, the method further includes detecting surface topography of a region of the surface that is in a vicinity of the optical axis of the camera, by:

detecting a spectrum of broadband light that is reflected from the region, using a spectrometer; and analyzing the detected spectrum, using the computer processor.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 3B is a schematic illustration of light being reflected from the surface of an object, in accordance with some applications of the present invention;

FIG. 5 is a graph showing the thickness of the lipid layer of the tear film as function of time, as measured in accordance with some applications of the present invention.

DETAILED DESCRIPTION OF EMBODIMENTS

Figure 1:
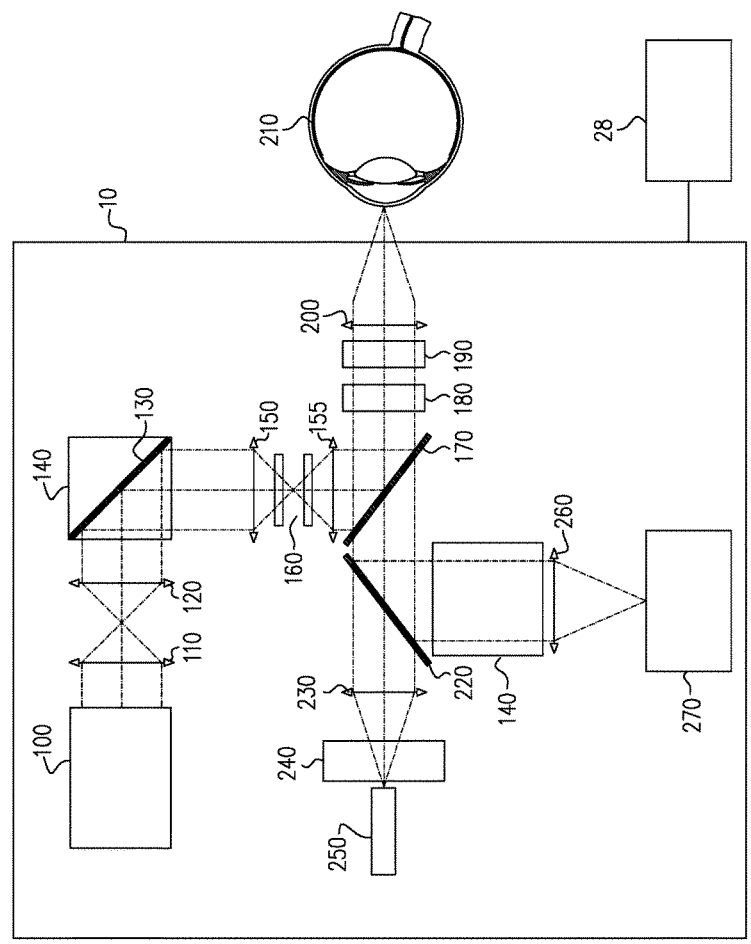
FIG. 1 is a schematic illustration of an optical system, in accordance with some applications of the present invention.

FIG. 1 shows a preferred embodiment according to the present invention in which an optical system 10 is used for measuring a biological tissue or a biological substance such as the lipid and the aqueous layers of an eye 210 over a large area. The system comprises a combination of a spectrometer 250 and/or an interferometer 140 and a color camera 270. It is well known that the contrast of the fringes ("spectral oscillations") originated from the aqueous layer is always considerably less than the contrast that can be obtained from the lipid layer. This fact is due to the anti-reflection coating effect caused by the mucus layer under the aqueous on the cornea and the Microvili scattering. However, this effect is much stronger in the visible range of the spectrum (400-800 nm) than in the near IR.

This effect can be overcome by combining (a) a spectrometer and/or an interferometer in the near infrared and visible region (NIR-VIS) and (b) a color camera. The spectrometer and/or interferometer provides the information of the fringes in the NIR and the VIS and the camera provides the information of the fringes in the VIS. (It is noted that the interferometer is typically used in conjunction with an imaging camera, such as camera 270.) From the information of the fringes in the NIR obtained by the interferometer and/or the spectrometer, the thickness of the aqueous layer is calculated. From the information of the fringes in the VIS by the camera, the thickness of the lipid layer is calculated. The information of the fringes in the VIS obtained by the interferometer and/or the spectrometer is also useful for calibrating the color camera. The accurate color of the point(s) where the interferometer and/or the spectrometer measures, can be calculated and the result can be used for calibrating the camera.

In the present embodiment which is described only for illustration, there are two paths; the illumination path and the imaging path. In the illumination path, the light emanates from a broadband light source 100 and is collimated by lenses 110 and 120. The light is folded by a mirror 130 or optionally by an interferometer 140 with movable mirrors. The interferometer can alternatively be disposed in the imaging path (to be described below) instead of the illumination path. (It is noted that FIG. 1 shows interferometer 140 disposed in both the illumination path and in the imaging path. However, typically, the interferometer is disposed in either the illumination path, or the imaging path.) The light is focused by the lens 150 on at least two grids 160 and collimated by the lens 155. The grids 160 are imaged on the cornea. The grids 160 are used for autofocusing and positioning the cornea in a certain determined distance from the system by examining the sharpness of the images of the grids on the cornea. The light passes through beam-splitter 170.

In another mode the autofocusing can be done directly on the image of features that exists on the cornea (e.g. lipids topography or simply the Iris). The light is directed to the cornea by a focusing optical element (e.g., a lens) 200. The focusing optical element 200 may be any kind of focusing optical element such as a compound lens, a Fresnel lens, Diffractive Optical element, etc. The light is focused to the approximated focal point of the concave mirror formed by the corneal surface such that it is reflected back at a small angle relative to the optical axis. The reflected light is gathered by the central part of the focusing optical element 200 or by an additional optical element placed in the central part of the focusing optical element 200. Optionally, other optical elements 180 may be disposed in the light path, such as a polarizer, which can contribute for proper background removal. For some applications, optical element 180 is a narrow aperture optical element, as described in further detail hereinbelow, with reference to FIG. 3A. A reticle 190 may also be disposed within the light path to serve as a target for directing the subject's gaze. In the imaging path, the light reflected from the cornea is partially reflected by the beam splitter 220 and focused on the camera 270, by lens 260, to image the cornea. The transmitted light is focused on the spectrometer 250, using lens 230, and analyzed.

In order to increase the accuracy of the autofocusing and/or to center the measured cornea relative to the optical axis of the camera and/or the spectrometer, a known pattern such as a circle or a square or some other structured light pattern may be projected onto the cornea using a projector. Due to its curvature, when the cornea is decentered relative to the optical axis, the image of the projected pattern is distorted. For some applications, this distortion is processed and used to center the cornea in real time.

As mentioned above, the information of the fringes in the NIR provided by the spectrometer and/or interferometer is used for calculating the thickness of the aqueous layer, and the information of the fringes in the VIS provided by the camera is used for calculating the thickness of the lipid layer. The information of the fringes provided by the interferometer and/or the spectrometer in the VIS is used for calibrating the color camera.

In an alternative mode the combined VIS-NIR spectrum can be analyzed using 3D electromagnetic simulation known in the art such as FTDT (Finite-Difference Time-Domain) or RCWT (Rigorous Coupled Wave Theory) or Green Function based calculations. The measured reflection of light from the cornea can be compared iteratively to a simulated measurement until a final fit is achieved for best corneal structure parameters. In such way both the thicknesses of the lipid layer, aqueous layer, mucin layer and microvilli roughness can be calculated simultaneously.

When the interferometer 140 is disposed in the imaging path before the camera 270 and the optical path difference (OPD) between the interferometer's mirrors is increased constantly, an interferogram is obtained for each point of the camera image. The Fourier transform of the interferogram provides the respective spectrum at each point of the image. The spectra can be analyzed for calculating the thickness of the lipid and aqueous layers. Since the spectrum in at least one point of the image is obtained also by the spectrometer, the spectra obtained by the spectrometer and the spectra obtained by the camera can be compared and the movements of the interferometer's mirrors can be calibrated.

As mentioned above, the interferometer 140 can also be disposed within the illumination path. In this embodiment, the light from the light source is modulated by a cosine function as a function of the OPD between the interferometer's mirrors. Fourier transforming the intensity of light at each point of the image as a function of the OPD also obtains the light spectra. The light spectra can be analyzed for calculating the thickness of the lipid and aqueous layers. Since the spectra of the image are also obtained by the spectrometer, the spectra obtained by the spectrometer and the spectra obtained by the interferometer can be compared and the movements of the interferometer's mirrors can be calibrated.

The provision of the interferometer 140, either in the illumination path or in the imaging path, and the combination of the interferometer, the spectrometer and the color camera, add some advantages:

When the OPD between the interferometer's mirrors is increased constantly, an interferogram is obtained for each point of the image at the camera. At each point of the image, the interferogram is recorded separately by the different color detectors of the color camera. Since the Fourier transform of the interferogram is the spectrum of the reflected light reaching the detector, all color detectors at each point of the camera can be calibrated absolutely using the spectral data obtained. The main advantage is that this calibration includes the overall spectral response of the whole system, the light source, the intermediate and the detector for each pixel of R/G/B differently.

The calibration of the response of the color detectors either by the spectrometer, the interferometer or both, is very critical for the lipid measurements where the sensitivity of the color change as a function of the lipid layer thickness is very high especially in the shorter wavelengths.

Another advantage of adding the interferometer and/or the spectrometer to the system is that the color detectors in the color camera integrate all reflected light, i.e. the specular and the diffuse light which may originate from much deeper interfaces. Thus, the thicknesses calculations based on the color camera alone may be inaccurate. However, in the spectrometer and the interferometer since the diffuse light contributes only to the DC level of the signal and not to the modulated signal, and thus can be omitted, this can increase the accuracy of the color and the thicknesses calculations based on it.

The combination of spectrometry and interferometry can also be used for the purpose of achieving a larger range of thickness measurements. In general, the spectrometer has a very good signal to noise ratio (SNR) but is limited to measuring thin films only due to its limitation on the spectral resolution. The high SNR enables measuring thin turbid layers very accurately (sub-nanometers). On the other hand the interferometer can measure several orders of magnitude higher and therefore its range can be complementary to the spectrometer range. In those cases where the interferometer detects thin turbid layer at a certain depth, the autofocus mechanism can shift the best focus position to this certain depth and the spectrometer can measure the reflectance from the thin turbid layer with higher SNR.

In still another embodiment, a spatial light modulator (SLM) can be integrated in one of the interferometer's arms. By applying several phase delays to the light by the SLM, the thicknesses of the thin layers can be calculated using Phase Shift Interferometry algorithms. The SLM may be based on moving micro-mirrors, LCD or any other method known in the art.

In order to increase the number of the points of the spectrometer's measurements, a deflecting element 240 may be disposed in the light path to the spectrometer. The deflecting element 240 deflects the incoming light from the cornea in such a way that at each time the light from different points of the cornea is analyzed by the spectrometer. In this embodiment, the calculations of the aqueous layer thickness are performed at several points and the calibration of the color camera is performed at several points of the image.

As mentioned above some other optical elements 180 may be added to the light path, such as polarizer, or a narrow aperture optical element, etc. The addition of a polarizer and/or a narrow aperture optical element may improve the signal in the following terms:

The non-specular reflected light is blocked.

The light reflected by the layers under the cornea may be blocked since these layers depolarize and rotate the polarization of illuminating light and/or are reflected in non-specular manner. In particular, the polarizer may block the light reflected from the iris of the eye.

Another working mode of the system uses a narrow band filter between the light source and the camera. In this case the image will have interference patterns in the form of fringes that are obtained by interfering light beams reflected from the different interfaces of the layers of the tear film. These layers may have thickness non-uniformities. The combination of non-uniformities of the layers thicknesses obtained from the interference patterns with the information obtained at specific discrete points from the accurate spectrometry measurements can give the following advantages:

1) a continuous full image with absolute thickness values per pixel;

2) the option to overcome the $2\pi$ ambiguity of the interference cycles.

For some applications of the present invention, thickness and/or spectral measurements of a thin biological layer are performed using one or more measurement parameters described hereinbelow. Typically measurements are performed on a thin biological layer in order to determine the thickness of the layer, and/or the changes over time of a parameter (such as, the thickness) of the layer. For some applications, thickness and/or spectral measurements of a thin biological layer, such as a tear film layer, are acquired using a spectrometer and/or an interferometer, using a measurement spot size of more than 40 microns and/or less than 240 microns (e.g., 40-240 microns), as described in further detail hereinbelow. For some applications, the measurements are performed over a time period of more than 20 ms and/or less than 300 ms (e.g., 20-300 ms), also as described in further detail hereinbelow.

It is noted that the term "spot size" when used in conjunction with spectrometric measurements should be interpreted as meaning the diameter of the area of the detected object from which reflected light is received by the spectrometer in a given spectrometric image. When used in conjunction with an interferometric measurement, the term "spot size" should be interpreted as meaning the diameter of the area of the detected object corresponding to pixels that are binned together with each other in the interferometric measurement. As noted hereinabove, typically the interferometer is used together with an imaging camera, such as camera 270. The term "sampling size" may be used interchangeably with the term "spot size".

The thin biological layer typically includes one or more sub-layers. For example, the tear film typically includes tear film inner layers, such as the lipid and/or the aqueous layers, and/or one or more delicate membranes, such as the basement membrane and/or the inner limiting membrane. A thin biological layer as described herein may include the tear film and/or any one of the aforementioned constituent layers of the tear film. For some applications, such measurements are performed using the optical system described hereinabove with reference to FIG. 1. For some applications, a combination of two or more measurements is performed on the tear film, e.g., using techniques described hereinabove. For example, a high quality and high resolution spectral and/or interferometric measurement of a single spot (or a plurality of spots) may be performed, together with high quality and large field-of-view imaging of the reflection from a given inner layer of the tear film. For some applications, measurements as described herein are performed using a spectrometer, an optical camera, an interferometer, and/or a different imaging device, without using other components belonging to the optical system shown in FIG. 1. Measurements are typically performed in order to determine clinical parameters that are indicative of the root cause of a dry eye diagnosis and/or the health of the tear film. For example, such parameters may include blink rate, tear break up time, variation of lipid thickness with time, lipid uniformity, aqueous layer thickness, evaporation rate, etc. For some applications, two or more of the following parameters are measured simultaneously: aqueous flow rate, aqueous layer thickness, lipid layer integrity, and evaporation rate.

Typically, interferometric and/or spectrometric measurements (such as aqueous flow rate measurements) are performed at a frequency of more than 2 (e.g., more than 5) and/or less than 50 measurements per second (e.g., 2-50, or 5-50 measurements per second). Further typically, such measurements are performed using a maximal value of irradiance of more than 4 and/or less than 20 mw/cm^2, e.g., between 4 and 20 mw/cm^2. This is because an irradiance of approximately 20 mw/cm^2 is the maximum permitted eye exposure in the visible wavelength range. At this level of irradiance, in order to provide a signal-to-noise ratio that is sufficient to provide an interference pattern that can be resolved, it is typically desirable that the interferometer and/or spectrometer spot size is at least 40 microns.

Further typically, for spectroscopic and/or interferometric measurements, it is desirable that the peak of the interference reflection as a function of the wavelength is similar over the entire measurement spot. Therefore, it is typically desirable that the change of the layer thickness within the measurement spot is less than approximately one-tenth of the mean wavelength. For example, for a broadband illumination with large spectrum of wavelengths which has a mean wavelength of 800 nm, it is desirable that within the measurement spot, the variation in the thickness of the layer that is being measured is less than 80 nm. It is typically a reasonable assumption that the thickness of the aqueous layer of the tear film has a uniformity of 330 nm per millimeter. Therefore, for some applications, when performing measurements on such a layer, a spot size of less than 240 microns is used (since 80 nm (the maximum desired variation in thickness) divided by 330 nm per millimeter (the variation per millimeter of the layer thickness) is 0.24 millimeters, i.e., 240 microns).

In view of the constraints described in the above paragraphs, typically when performing a thickness and/or a flow measurement on the aqueous layer based on an interference signal (e.g., using an interferometer and/or using a spectrometer), a spot size of more than 40 microns, and/or less than 240 microns (e.g., 40-240 microns) is used.

Figure 2:
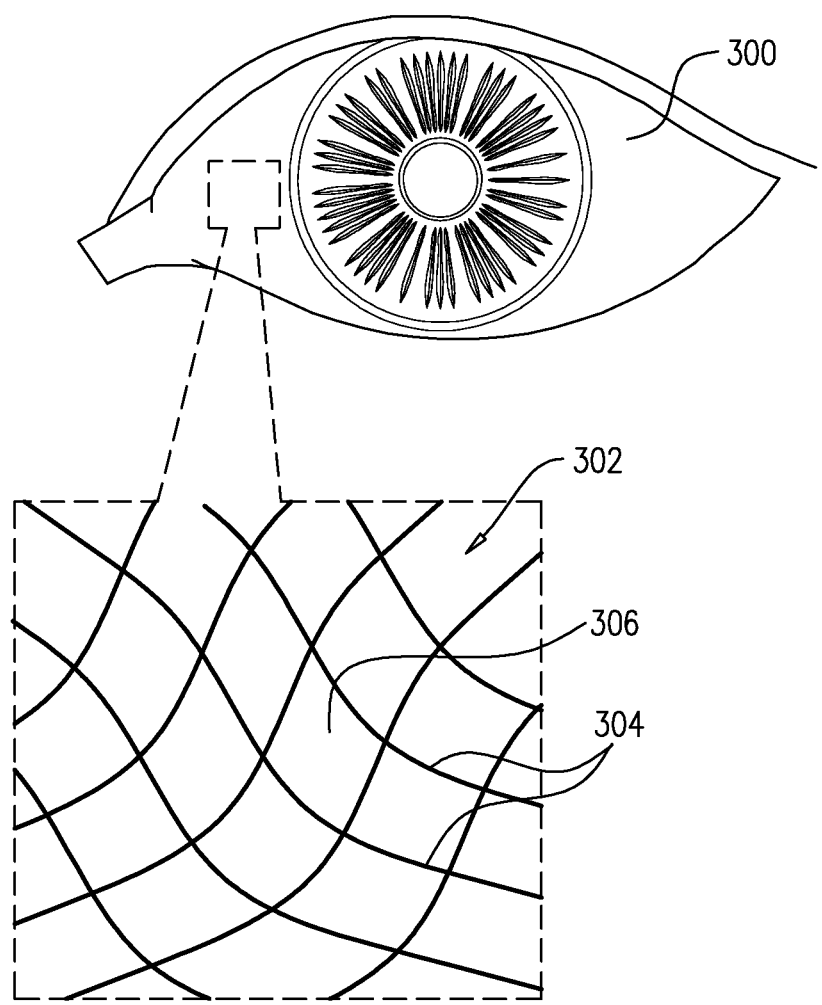
FIG. 2 is a schematic illustration of a subject's eye, the lipid layer of the tear film of the subject's eye including a collapsed region upon which measurements are performed, in accordance with some applications of the present invention.

Reference is now made to FIG. 2, which is a schematic illustration of a subject's eye 300, the lipid layer of the tear film of the subject's eye including a collapsed region 302, upon which measurements are performed, in accordance with some applications of the present invention. Breakup of a layer's integrity, for example, the collapse of the continuity of the thin lipid layer of the subject's tear film may occur periodically, and natural mechanisms, such as the blinking, may repair the film. In accordance with some applications of the present invention, parameters are measured that relate to the collapsed lipid layer of the subject's tear film. Many mechanisms can lead to a breakup, especially in a complex multi layers fluid such as the tear film.

Normally the collapse of the continuity of the thin lipid layer involves a local collapse of an underlying layer (such as the aqueous layer), or the absence of a mucin interface layer at a specific location. In such cases, portions of the lipid layer that overlie the collapsed underlying layer may form a net structure, as shown in FIG. 2. The net structure includes curves 304 of the net which have collapsed into the space left by the collapsed underlying layer(s), and areas 306 between the curves of the net which have not collapsed. (It is noted that, for some applications, collapsed portions of the lipid layer form shapes other than that which is schematically illustrated in FIG. 2) In order to perform measurements on region 302, an imaging system with high resolution and with a small measurement spot size is typically used. Typically the spot size is constrained by the following constraints:

(a) It is desirable that the spot size be sufficiently small such that the illumination integration within the spot area will be sensitive to the development of new collapsed curves, and/or changes to the area of collapsed curves 304 relative to the total area that is within the spot. Typically, the curves of the net have a width of between 10 and 30 microns, and the spectrometer and/or interferometer is sensitive to changes that encompass 10 percent of the area of the spot. Therefore, typically the spot size is less than 300 microns. Typically, the spot size is less than 240 microns, due to the non-uniformity of the aqueous layer, as described hereinabove.

(b) It is desirable that the spot size be sufficiently large so as to capture curves of the net, if such curves are present. Therefore, it is typically desirable that the spot size is greater than 100 microns.

In accordance with the description hereinabove, typically spectrometric measurements are performed using a measurement spot size that is constrained by one or more of the following considerations:

In order to perform thickness measurements on the aqueous layer of the tear film, using a spectrum of wavelengths having a mean wavelength of approximately 800 nm, the spot size is typically less than 240 microns. Typically, this is such that the change of the layer thickness within the measurement spot size is less than approximately one-tenth of the mean wavelength.

In order to perform aqueous flow rate measurement, a minimal spot size of 40 microns is typically used, in order to provide a signal-to-noise ratio that is sufficient to provide an interference pattern that can be resolved.

In order to perform integrity measurements on the lipid layer of the tear film, a minimal spot size of 100 microns is used, in order to be sufficiently large so as to capture curves of the net that is formed by the lipid layer when the lipid layer is collapsed. Furthermore, in order to be sufficiently small such that the illumination integration within the spot area will be sensitive to the development of new collapsed curves, and/or changes to the area of collapsed curves 304 relative to the total area that is within the spot, the spot size is typically less than 300 microns, e.g., less than 240 microns.

Accordingly, in accordance with some applications of the present invention thickness and/or spectral measurements of a tear film are acquired using a measurement spot size of more than 40 microns (e.g., more than 100 microns), and/or less than 300 microns (e.g., less than 240 microns), for example, 40-300 microns, or 100-240 microns, such a spot size being suitable for most of the measurement requirements described above. Typically, the measurements are acquired using a spectrometer and/or an interferometer. For some applications, optical system 10 as shown in FIG. 1 is used.

Figure 3A:
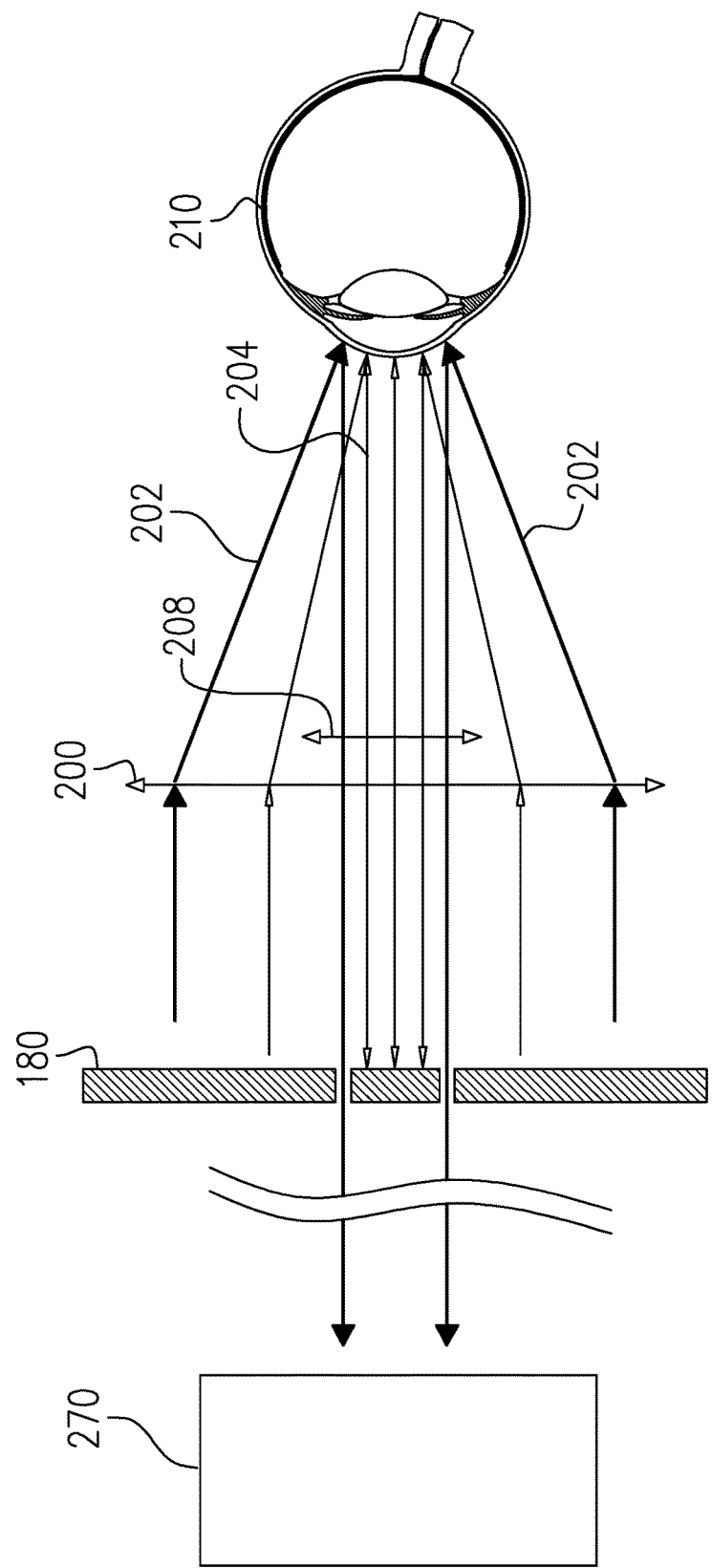
FIG. 3A is a schematic illustration of an optical element of an optical system, in accordance with some applications of the present invention.

Reference is now made to FIGS. 3A and 3B, which are schematic illustrations of eye 210 being illuminated, in accordance with some applications of the present invention. As described hereinabove, for some applications, in addition to performing spectroscopic and/or interferometric measurements on the tear film, the tear film is imaged using camera 270 of optical system 10 (shown in FIG. 1). For some applications, the optical system has a large field of view but with fine resolution, for example, in order to capture local collapse phenomena of one or more of the underlying layers.

Typically, a curved surface of an object, e.g., the surface of the cornea of eye 210, is illuminated from a broad angle of incidence (e.g., an angle of incidence of more than 50 degrees relative to the optical axis of camera 270). For some applications, the surface is illuminated using a point source. For some applications, the optical system is configured to perform ray tracing such that each angle out of the overall angle that is directed to the curved surface (e.g. the surface of the cornea of the eye) is directed toward a respective portion of the curved surface. Light is thereby focused onto the surface (e.g., using lens 200), such that a respective narrow angle illumination beam is focused upon respective portions of the surface, as shown schematically in FIG. 3A. For some applications, before passing through lens 200, the incident light passes through a collimator, such that light beams that are incident upon lens 200 are parallel to each other, as shown schematically in FIG. 3A.

Light is collected from the object using a narrow-aperture optical element 180. Typically, the narrow-aperture optical element collects light beams that define an angle of more than 1 degree (e.g., more than 2 degrees) and/or less than 3 degrees, e.g., an angle of between 1 and 3 degrees, or an angle of between 2 and 3 degrees.

For some applications, the optical system includes an objective lens 208 that is configured to collect and collimate the rays reflected from the curved surface of the object, such that the rays are directed toward element 180. In addition, for some applications, element 208 acts as first narrow aperture, by only collecting rays within a narrow angle. Typically, the rays then pass through optical element 180, which acts as an additional narrow aperture.

For example, as shown in FIG. 3A, light is directed toward eye 210 from a broad angle of incidence. Optical element 180, which defines a narrow aperture, is disposed in any relevant conjugate plane, and is used to block light from that reflects from the surface other than light within a narrow angle. In general, for such applications, optical element 180 is an apodizer. For example, optical element may be an annular filter. Typically, at respective times, optical element 180 is used to allow reflected narrow-angle beams to pass through to the camera from respective angles of reflection, and to block reflected light from being imaged by the camera outside of the reflected narrow-angle beam. Thus, at respective times, respective circular rings of the surface are imaged by the camera.

For some applications, illuminating the object (e.g., the eye) from a broad angle of incidence, but such that a respective narrow angle illumination beam is focused upon respective portions of the surface, and collecting the light using a light collection aperture having a narrow angle opening, enhances the ratio between the collected quantity of specular light and the collected quantity of non-specular light due to surface topography. This is due to the fact that the quantity of non-specular light that is collected is proportional to the solid angle of the collecting optical system and its radiance does not depend on the angle of the reflecting surface relative to the angle of the illumination beam. By contrast, the quantity of specular light that is collected depends on the solid angle of divergence of the beam itself (assuming that the solid angle of the collecting optical system is larger than the solid angle of divergence of the beam), and it also depends on the angle of the reflecting surface relative to the angle of illumination beam and the optical axis of the collecting system.

Typically light that is reflected from the surface of the object is narrowed by narrowing the angle of the reflected light using optical element 180, which is disposed at the imaging or collecting optical system and/or any conjugate plane. The optical system is typically set to a narrow angle using the techniques described above, such that the specular light is transmitted through optical element 180, while most of the non-specular light is blocked, and thus extra sensitivity to specular light loss is achieved. When a gradual change in surface topography is present (due to sub-micron level variations in the height of the surface), a portion of the specular light is reflected in a different direction from the rest of the specular light, such that the portion of the specular light is not collected by the aperture, and the amount of collected specular light is reduced. For some applications, the system is typically able to detect such sub-micron level variations in the height of the surface (e.g., sub-micron level variations in the height of the tear film surface) by detecting darkened regions in the received specular light.

Typically, a detectable change in the light that is received by the camera is caused by a change in the surface angle of the object that corresponds to more than 10 percent of the angle of the light beam that that is received by the camera. Since the narrow-aperture optical element is configured to collect a light beam that defines an angle in the order of 1-3 degrees, the system is sensitive to changes in the angle of the surface of less than 0.1-0.3 degrees. Typically, the resolution of the optical system is such that the camera pixel size corresponds to a distance of 5 microns across the surface of the object. Therefore, typically, the system is able to detect surface height variations of less than 25 nm (e.g., 10-25 nm), which correspond to a surface angle of 0.1-0.3 degrees over a 5 micron distance.

The above technique and system is schematically illustrated in FIGS. 3A and 3B. As shown in FIG. 3A, the surface of the cornea of eye 210 is illuminated by a broad angle illuminating beam using focusing optical element(s) (e.g., lens 200) that are designed such that, out of the overall angle of light rays that is directed to the cornea, rays with from respective angles are directed toward respective portions of the cornea. Due to the angle of the surface, at a given location, specular light rays 204 that are reflected from the cornea are collected and collimated by objective lens 208. The collected light passes through narrow aperture optical element, such that only the reflected light from narrow angle beam 202 passes through the optical element. The reflected light from narrow angle beam 202 is directed by the rest of the optical system towards camera 270, such that the camera images a circular ring on the corneal surface upon which narrow angle beam 202 was incident. In this configuration, most of the non-specular light is blocked.

FIG. 3B illustrates the reflection structure of the specular light in the presence of a pit or a bump on the portion of corneal surface of eye 210 upon which narrow angle beam 202 was incident. (It is noted that, for illustrative purposes, lens 200 is not shown in FIG. 3B.) The illumination light beam 202 illuminates the portion of the surface of the cornea. Most of the specular light rays that reflect from the portion of the surface are reflected toward objective lens 208 and then toward the aperture in narrow aperture optical element 180. However, when a pit 212 is present, a portion 206 of light rays are reflected to different angles and they are not collected by objective lens 208, and/or narrow aperture optical element 180. Therefore, there is a darkened region corresponding to this location on the image. In response to detecting darkened regions of the image of the surface, computer processor 28 (FIG. 1) determines the surface topography of the tear film (typically, to the sub-micron level).

In accordance with the description of FIGS. 3A-3B, the insertion of optical element 180 in the imaging path may increase the selectivity of imaging to specular object surface reflection. In this manner, the sensitivity to lost specular light at a given radial position can be emphasized.

It is noted that, at the center of the surface of the object that is imaged (e.g., at the center of the cornea of eye 210), the system is typically unable to detect surface topography using the above-described technique, since all of the reflected specular light is typically received by narrow-angle collecting optical element 208 and/or by narrow aperture optical element 180 (when the narrow aperture is in the central portion of the optical imaging plane). Therefore, typically, optical system 10 utilizes spectrometer 250 (FIG. 1) to measure the spectrum of the broadband light in the central region of the surface of the object (e.g., the cornea of the eye). The measured spectrum is analyzed, for example, by comparing the spectrum to a model of electromagnetic wave simulation. Typically, the computer processor is configured to detect a non-flat topography (e.g., due to collapse of the lipid layer as described hereinabove) in the central region of the object, by analyzing the measured spectrum. In this manner, the specular normal incidence is measured using the spectrometer, while the imaging system is configured to have high camera sensitivity to the topography of the outer regions of the surface, using the techniques described herein, due to the oblique incident light.

For some applications, an RGB camera (e.g., camera 270) is used to detect a non-flat topography (e.g., due to collapse of the lipid layer as described hereinabove) in the central region of the object. Typically, collapsed regions of the lipid layer of the tear film (which may form the appearance of a net on the tear layer, as described hereinabove) changes the color of the lipid layer. This is because the homogeneous area has a color that matches the average lipid thickness, while the collapsed regions contribute a different color ratio. This contribution is proportional to the area of the collapsed regions. For some applications of the present invention, changes in the area of the collapsed regions relative to the total area that is imaged is determined by measuring a change of the lipid layer's color as a function of time using images obtained using an RGB camera. For some applications, optical system 10 is configured to detect that that the lipid layer has a thickness of less than a given thickness (e.g., a thickness of less than between 20 nm and 0 nm), by detecting that a region of the RGB image is achromatic. Typically, using the techniques described herein, the computer processor of the optical system is configured to distinguish between darkening due to color based lipid thickness and darkening due to scattered light that is caused by surface topography.

In order to measure spectral measurements, such as the change of the color due to a layer thickness, a camera is used that has high spectral resolution qualities. As described hereinabove, when the collapsed lipid layer forms a net structure, curves of the net of the lipid layer typically have widths of 10-30 microns. Each R, G, or B sub-pixel of the camera typically has a pixel size that is less than 15 microns (e.g., less than 10 microns), such that the resolution of each of the R, G, and B detectors is smaller than the thickness of the curves of the net. Further typically, the point-spread function of the RGB camera for each of the colors is less than 15 microns (e.g., less than 10 microns). For some applications, the RGB camera's modulation transfer function is higher than 0.9. Typically, by virtue of having a modulation transfer function at such a value, the camera is configured to detect a color variation of about 1% between adjacent pixels, and/or is configured to detect at least a single gray level difference at 10 bit information.

Typically, the thicknesses of respective layers of the tear film vary over time due to a number of different mechanisms. For example, the tear film aqueous layer evaporates while the eyelids are open, thickens due to tearing, and drains if overflow take place. For some applications, a tear film measuring system (such as system 10, or a different system that may include any one of an interferometer, a spectrometer, and/or a camera) acquires measurements over a period of time, and parameters of the tear film are acquired by averaging the acquired measurements. For example, the thickness of the aqueous layer of the tear film as a function of time, the flow rate of the aqueous layer, and/or the evaporation rate of the aqueous layer may be detected using spectroscopic and/or interferometric measurements. As described in further detail hereinbelow, for some applications, a plurality of measurements are acquired over a time period of more than 1 second and/or less than 10 seconds (e.g., less than 5 seconds), e.g., 1-10 seconds, or 1-5 seconds. Typically, the measurement time of each of the measurements is more than 20 milliseconds and/or less than 300 milliseconds, e.g., 20-300 milliseconds.

In addition, since the rate of thickness change, and/or the evaporation rate of the aqueous layer changes with time, and there is also a liquid flow on top of the cornea, the interferometer and/or spectrometer acquires measurements at a minimal rate of measurements per second, as described in further detail hereinbelow. Furthermore, since for healthy people the rate of thickness change, and/or the evaporation rate is typically only several nanometers per second or lower, the interferometer and/or spectrometer is configured to preserve the repeatability of the measurements on a sub-nanometer level.

As described above, the tear film aqueous layer evaporates while the eyelids are open, thickens due to tearing, and drains if overflow take place. Typically, the period of time over which measurements are acquired is long enough such as to limit the effect of random fluctuations in the measured parameter, but short enough to exclude biological changes. For example, measurements of the thickness of a layer of the tear film may be acquired over a period of more than 1 second and/or less than 10 seconds (e.g., less than 5 seconds), e.g., 1-10 seconds, or 1-5 seconds. During this period, several of the aforementioned mechanisms may occur. Typically, system 10 is configured to differentiate between the various mechanisms and to thereby determine a parameter that relates to a particular mechanism.

Typically, a subject maintains their eye in a stable position, while focusing on a specific target, for a period of between several milliseconds and several seconds. Therefore, in order to perform each of the measurements such that the eye is in a stable position for the duration of the measurement, a measurement time of less than 300 milliseconds is used for each measurement.

Furthermore, measurement of liquid dynamics (e.g., flow rate, rate of thickness change, and/or evaporation rate) is typically performed in a manner that is such as to reduce smearing of the spectroscopic and/or interferometric signal due to a change in the uniformity of the layers of the tear film. Typical flow rates 1-2 seconds after a blink are in the order of 1 mm per second. Assuming that the non-uniformity per millimeter of the layer thickness is less than 200 nm, then in order to obtain a non-smeared signal using an average wavelength of 800 nm, at least two measurements per second are typically acquired. For some applications, in order to distinguish between different dynamic parameters, such as the flow rate and the evaporation rate, at a single static location on the eye, at least 20 measurements per second are acquired.

The rate of thickness change, and/or the evaporation rate of the aqueous layer is determined by the gradient of the thickness of the aqueous layer as a function of time. Since the gradient itself varies due to different conditions of the lipids integrity, the level of humidity, the temperature and air flow, the slope is a momentary characteristic of the aqueous layer. For some applications, the spectrometer and/or interferometer is configured to acquire measurements at a frequency that is such that the gradient can be determined. For example, for dry eye patients that have a fast rate of thickness change, and/or evaporation rate and a blink rate in the order one blink every 5 seconds or faster, measurements are acquired at a frequency of at least 5 measurements per second.

Evaporation itself during a given measurement can smear the measurement, if a significant thickness change occurs during the measurement. Typically, the maximal allowed change of the thickness of the aqueous layer within one measurement should be less than one tenth of the average wavelength. For an average wavelength of 800 nm, the allowed change in thickness during the measurement is 80 nm. Since dry eye patients can have evaporation rates of 250 nm per second, typically the duration of each measurement is less than 300 msec. In order to provide a sufficient signal-to-noise ratio, the duration of each measurement is typically greater than 20 milliseconds. Thus, typically, each measurement is between 20 and 300 milliseconds in duration, and there are more than 4 and/or less than 50 (e.g., 4-50) measurements per second.

Figure 4:
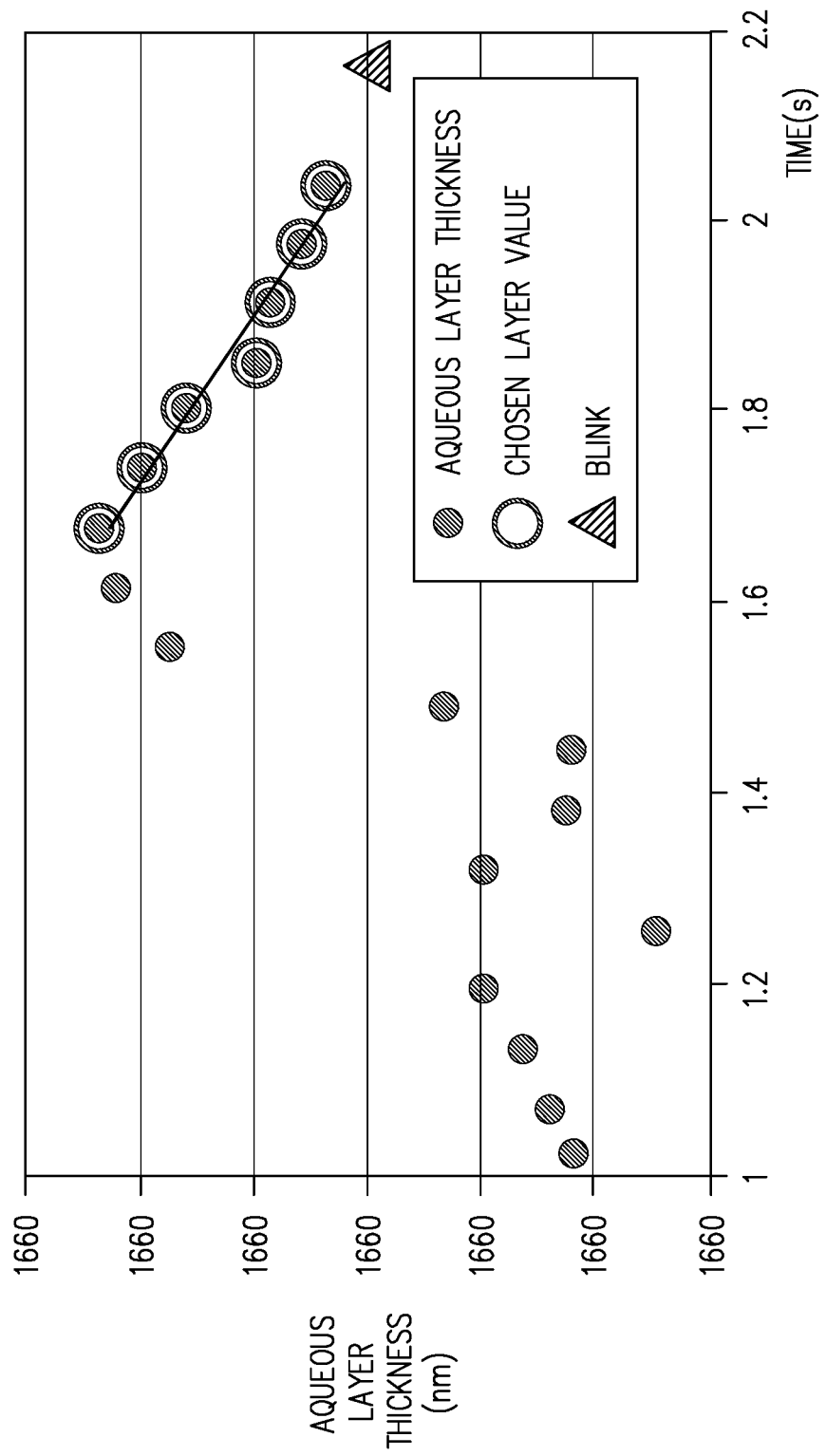
FIG. 4 is a graph showing a typical variation of the thickness of an aqueous layer as a function of time, as measured in accordance with some applications of the present invention.

Reference is now made to FIG. 4, which is a graph showing a typical variation of the thickness of an aqueous layer as a function of time, as measured in accordance with some applications of the present invention. For some applications, the rate of thickness change and/or the evaporation rate of the aqueous layer is extracted from the curve shown in FIG. 4 by selecting a portion of the curve within which there is a linear correlation between the thickness of the aqueous layer and time, and determining the gradient of the curve within that portion. For some applications, in order to determine the rate of thickness change, and/or the evaporation rate, a portion of the curve that terminates at a given time prior to a blink (e.g., 0.1 seconds prior to a blink) is selected. For some applications, measurements are performed within a period of 2 seconds (e.g., between 0.2 seconds and 1 second) prior to a blink. For example, a time period starting 0.5 seconds before a blink and terminating 0.1 seconds before the blink may be selected. Alternatively, a portion of the curve is selected irrespective of the temporal proximity of the section of the curve to a blink, or a portion of the curve is selected based on the portion starting a given time after a blink. For some applications, a portion of the curve is selected in response to (a) the gradient within the portion being negative (which implies layer thinning), and (b) the correlation value ($R^2$) of the curve being greater than a threshold, such a greater than 0.8, or greater than 0.9. For some applications, only a portion of the curve that corresponds to four or more measurements and that satisfies the aforementioned criteria is selected for determining the rate of thickness change, and/or the evaporation rate. (It is noted that for some applications, algorithmic operations that are the equivalent of performing the above steps are performed, without actually plotting a curve as shown in FIG. 4.)

For example, as shown in FIG. 4, for the portion of the curve between approximately 1.65 seconds and 2.05 seconds, the curve corresponds to four or more measurements, has a negative gradient, and has a correlation rate of more than 0.9. This portion of the curve terminates shortly before a blink at around 2.15 seconds. Therefore, the rate of thickness change, and/or the evaporation rate may be determined by determining the gradient of the curve within that portion of the curve. As shown, in the graph of FIG. 4, seven aqueous layer thickness data points were selected, as indicated by the data points with a circle around them. By contrast, other data points do not satisfy the aforementioned criteria, for example, due to disruptive events (e.g., fast fluid flow, tearing, partial blinks, or eye movements).

Reference is now made to FIG. 5, which is a graph showing the thickness of the lipid layer of the tear film as function of time, as measured in accordance with some applications of the present invention.

For some applications of the present invention, the stability of a biological layer, such as a layer of the tear film (e.g., the lipid layer) is used to determine the health of the layer, and/or the health of the tear film. For some applications, repeated measurements are performed on such a layer in order to determine the stability level of the layer, and the health of the layer, and/or the health of the tear film is determined in response thereto. For example, spectrometric and/or interferometric measurements as described herein may be performed. For some applications, optical system 10 (shown in FIG. 1) is used to perform such measurements.

For some applications, the stability level of the layer is determined by determining a ratio between the variance or standard deviation of a parameter of the layer (such as, the layer thickness) and the average values of the parameter. Since, for example, the variance or standard deviation of the layer thickness is affected by the actual value of the layer thickness, determining the aforementioned ratio is a way of standardizing the variance or standard deviation measurements. For example, for the measurements of the lipid layer thickness, shown in FIG. 5, the standard deviation of the measurements is 1.4 nm, and the average thickness is 31.6 nm. Therefore, in accordance with the techniques described herein, the layer stability is defined as 4.4 percent (i.e., the standard deviation of the thickness as a percentage of the average thickness).

For some applications, while measuring the stability, disruptive events such as blinking are identified, and measurements are classified in relation to these events. For example, the flow rate of a substance within a layer is likely to change dramatically following such a disruptive event and to settle thereafter. Therefore, for some applications, in order to determine the intrinsic stability of a parameter of a layer (i.e., the stability of the layer in the absence of the effects of disruptive events), measurements of the parameter that are performed soon after such an event are discarded. For example, for determining the stability of a parameter (e.g., thickness) of a layer of the tear film (e.g., the lipid layer) measurements that are acquired immediately after a blink are not used, and measurements that are acquired shortly before a subsequent blink are used. It has been found by the inventors of the present application that for healthy patients, the normal intrinsic stability parameter variations of the thickness of the lipid layer of the tear film are typically smaller than 10% (e.g. smaller than 5%), whereas for non-healthy patients intrinsic stability parameter variations are substantially higher.

Breakup of a layer's integrity can happen from time to time and natural mechanisms, such as blinking, may repair the layer subsequent to the breakup. Many mechanisms can lead to break up the layer's integrity, especially in a complex multi layers fluid, like the tear film. Measuring the time from a resetting event, such as a blink, to the breakup event provides a characteristics parameter of the layer integrity.

For some applications of the present invention, a breakup event is identified, in response to identifying that the layer thickness at a specific area crosses a predefined threshold. In response thereto, a breakup time is determined by determining the time that elapsed since the previous resetting event (e.g., the previous blink) until the breakup. For some applications, the level of health of the layer of the tear film, and/or a level of health of the tear film is identified in response to the determined breakup time. Typically, only the first breakup after the resetting event is considered for breakup time calculation. For some applications, the aforementioned threshold is defined relative to a moving average of the layer's thickness over a previous given time period. For example, the moving average may be determined based upon measurements performed over the previous 1 second, or over the previous 0.5 seconds. Typically, the moving average is determined based upon measurements performed over a period of time that is between 0.5 and 1 second. For some applications, the threshold is defined as a percentage of the moving average. For example, the threshold may be 90 percent, or 95 percent of the moving average, such that if the thickness falls by 10 percent or 5 percent relative to the moving average, a breakup event is identified as having occurred.

For example, the curve shown in FIG. 5 is a moving threshold, which is based upon a moving average of the lipid layer thickness, based upon the previous 0.6 seconds of measured data. For the threshold shown in FIG. 5, the threshold is 90 percent of the moving average. At approximately 18.7 seconds, there is a blink, which is a disruptive event. Subsequently, at approximately 19.4 seconds, 0.685 seconds after the blink, the measured thickness drops below the threshold curve, which is indicative of a breakup event having occurred. Hence, the breakup time is 0.685 seconds.

For some applications, in identifying breakup events, the shifting of fluid within a layer is accounted for. Since the fluid is constantly shifting, there is a thickness change over time. It is noted that the characteristic span of thickness values across a wide enough area is typically similar at different points in time. However, the thickness in a specific area can change dramatically if a breakup event occurred within the area, or if a collapsed area spreads into the measurement area from the surrounding areas. Therefore, for example, the thicknesses of surrounding areas may be taken into account, in order to determine whether a breakup event has occurred in a given area. For example, the variance in the thicknesses of areas in the vicinity of the given area may be compared to the variance in the given area, and a breakup event may be confirmed as having occurred at least partially in response thereto.

For some applications, breakup events are detected in response to detecting the histogram of the ratios between R, G, and B of the color camera at respective areas. Since pixel colors have a relation to thickness, the histogram of the ratios between R, G, and B of the camera at an area that experienced a breakup event undergoes a substantial change, whereas at areas that did not experience a breakup event the histogram remains substantially the same.

For some applications, the layer stability is determined at least partially in response to determining the number of breakup events that occur between resetting events.

Typically, the layer stability is determined by performing depth measurements on fewer than 10, e.g., fewer than 5 areas within the layer. Typically, each such depth measurement is averaged over an area extending over more than 0.1 square millimeters and/or less than 0.2 square millimeters, e.g., 0.1-0.2 square millimeters. Typically, thickness measurements are performed at time intervals of more than 20 msec, and/or less than 300 msec (e.g., every 20-300 msec) in order to determine such breakup events.

Applications of the invention described herein can take the form of a computer program product accessible from a computer-usable or computer-readable medium (e.g., a non-transitory computer-readable medium) providing program code for use by or in connection with a computer or any instruction execution system, such as a computer processor 28 (FIG. 1), which may be in communication with optical system 10. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor (e.g., computer processor 28) coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object oriented programming language such as Java, Smalltalk, C++ or the like and conventional procedural programming languages, such as the C programming language or similar programming languages.

It will be understood that the algorithms described herein, can be implemented by computer program instructions. These computer program instructions may be provided to a processor of a general purpose computer, special purpose computer, or other programmable data processing apparatus to produce a machine, such that the instructions, which execute via the processor of the computer (e.g., computer processor 28) or other programmable data processing apparatus, create means for implementing the functions/acts specified in the algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the algorithms described in the present application.

Computer processor 28 is typically a hardware device programmed with computer program instructions to produce a special purpose computer. For example, when programmed to perform the algorithms described herein, computer processor 28 typically acts as a special purpose tear-film-analysis computer processor. Typically, the operations described herein that are performed by computer processor 28 transform the physical state of a memory, which is a real physical article, to have a different magnetic polarity, electrical charge, or the like depending on the technology of the memory that is used. For some applications, operations that are described as being performed by a computer processor are performed by a plurality of computer processors in combination with each other.

It should be noted that features that are described with reference to one or more embodiments are described by way of example rather than by way of limitation to those embodiments. Thus, unless stated otherwise or unless particular combinations are clearly inadmissible, optional features that are described with reference to only some embodiments are assumed to be likewise applicable to all other embodiments also.

The invention claimed is:

1. A system for performing tear film structure measurement, the system comprising:
   a broadband light source configured to illuminate the tear film;
   a spectrometer for measuring respective spectra of reflected light from at least one point of the tear film;
   a color camera configured for large field of view imaging of the tear film so as to obtain color information for all points of the tear film imaged by the color camera; and
   a processing unit coupled to the camera and to the spectrometer and configured for (i) calibrating the camera at the at least one point measured by the spectrometer so that the color obtained by the camera at said at least one point matches the color of the spectrometer at the same point, and (ii) determining from the color of respective points of the calibrated camera thicknesses of one or more layers of the tear film at the respective points.

2. The system according to claim 1, further comprising a flat objective Fresnel lens that is configured to converge a large range of angles to a point and is disposed a short distance from the tear film.

3. The system according to claim 1, further comprising an autofocusing mechanism for focusing the color camera and the spectrometer.

4. The system according to claim 1, further comprising a mechanism for centering a cornea of the subject onto optical axes of the spectrometer and the color camera, the mechanism comprising a projector that is configured to project a given pattern onto the subject's cornea.

5. The system according to claim 1, wherein the processing unit is further configured to compute respective rates of change of thicknesses of the one or more layers of the tear film at different points along the tear film obtained over a known time interval.

6. The system according to claim 1, further comprising one or more optical elements selected from the group consisting of: lenses, Fresnel lenses, annular aperture filters, polarizers, spatial light modulators (SLMs), and diffractive optical elements (DOEs).

7. The system according to claim 1, further comprising an interferometer having a pair of mirrors disposed in a path selected from the group consisting of: an illumination path of the system and an imaging path of the system, and configured to modulate the spectrum of the light source by changing the optical path difference between the mirrors.

8. The system according to claim 7, wherein the processing unit is coupled to the interferometer and configured for (i) calibrating consecutively the interferometer by computing the optical path difference between the mirrors of the interferometer at at least one of the points measured by the spectrometer, (ii) using the calibrated interferometer to modulate the spectrum of the light source by changing the optical path difference between its mirrors, (iii) obtaining a calibrated interferogram at respective points of the tear film, and (iv) using the calibrated interferogram to determine thickness of one or more layers of the tear film at the respective points.

9. The system according to claim 1, wherein the spectrometer further includes a deflecting element for scanning different tear film locations.

10. The system according to claim 9, further comprising a narrow band filter between the light source and the camera for producing interference fringe patterns characteristic of different layers of the tear film.

11. The system according to claim 10, wherein the spectrometer is used to correlate a fringe pattern in a known location or pixel with a respective thickness of each layer of the tear film and thereby derive the respective thickness of each layer of the tear film without scanning the tear film.

12. The system according to claim 1, wherein the spectrometer is configured to measure the respective spectra of reflected light from the at least one point of the tear film using a measurement spot size of between 40 microns and 300 microns.

13. The system according to claim 12, wherein the spectrometer is configured to measure the respective spectra of reflected light from the at least one point of the tear film using a measurement spot size of between 100 microns and 240 microns.

14. A method for performing tear film structure measurement, the method comprising:
illuminating the tear film with a broadband light source;
using a spectrometer to measure respective spectra of reflected light from at least one point of the tear film;
imaging on a color camera a large field of view image of the tear film so as to obtain color information for all points of the tear film;
calibrating the camera at the at least one point measured by the spectrometer so that the color obtained by the camera at said at least one point matches the color of the spectrometer at the same point; and
determining from the color of respective points of the calibrated camera thicknesses of one or more layers of the tear film at the respective points.

15. The method according to claim 14, further comprising computing respective rates of change of the thicknesses of the one or more layers of the tear film at different points along the tear film obtained over a known time interval.

16. The method according to claim 14, further comprising:
(i) using a narrow band filter to obtain an interference pattern due to thickness non uniformity of the one or more layers of the tear film;
(ii) determining absolute values of the thicknesses of the one or more layers of the tear film at the overlapping locations of the interference pattern and spectrometer measurement points;
(iii) applying the absolute values at overlapping locations to determine the absolute values of the thicknesses at neighboring pixels that also have interference patterns.

17. The method according to claim 14, further comprising using electromagnetic simulation in order to fit measurement results to a biological model of stack of tissues and liquid layers.

18. The method according to claim 14, further comprising autofocusing the color camera and the spectrometer.

19. The method according to claim 14, further comprising:
Fourier transforming the spectra of the reflected light so as to obtain, for each of point measured by the spectrometer, a respective interferogram; and
using the interferograms to determine the thickness of the one or more layers of the tear film at the corresponding point.

20. The method according to claim 19, further comprising computing a respective rate of change of the thicknesses of the one or more layers of the tear film at different points along the tear film obtained over a known time interval.

21. The method according to claim 14, further comprising modulating a spectrum of the light source by changing an optical path difference between a pair of mirrors of an interferometer.

22. The method according to claim 21, further comprising:
(i) calibrating the interferometer by computing the optical path difference between the mirrors of the interferometer at at least one of the points measured by the spectrometer,
(ii) using the calibrated interferometer to modulate the spectrum of the light source by changing the optical path difference between the mirrors of the calibrated interferometer,
(iii) using the measured reflected light to obtain a calibrated interferogram at respective points of the tear film, and
(iv) using the calibrated interferogram to determine a thickness of the one or more layers of the tear film at the respective points.

23. The method according to claim 14, wherein using a spectrometer to measure respective spectra of reflected light from at least one point of the tear film comprises using a measurement spot size of between 40 microns and 300 microns.

24. The method according to claim 23, wherein using a spectrometer to measure respective spectra of reflected light from at least one point of the tear film comprises using a measurement spot size of between 100 microns and 240 microns.

* * * * *